US009414825B2

(12) United States Patent
Takahashi

(10) Patent No.: US 9,414,825 B2
(45) Date of Patent: Aug. 16, 2016

(54) CLOSURE DEVICE

(71) Applicant: Olympus Corporation, Tokyo (JP)

(72) Inventor: Shinji Takahashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/515,050

(22) Filed: Oct. 15, 2014

(65) Prior Publication Data
US 2015/0057704 A1 Feb. 26, 2015

Related U.S. Application Data

(63) Continuation of application No. PCT/JP2013/068005, filed on Jul. 1, 2013.

(60) Provisional application No. 61/694,935, filed on Aug. 30, 2012.

(51) Int. Cl.
A61B 17/08 (2006.01)
A61B 17/00 (2006.01)
A61B 17/10 (2006.01)

(52) U.S. Cl.
CPC ............ *A61B 17/0057* (2013.01); *A61B 17/08* (2013.01); *A61B 17/10* (2013.01); *A61B 2017/0061* (2013.01); *A61B 2017/00584* (2013.01); *A61B 2017/00623* (2013.01)

(58) Field of Classification Search
CPC ........... A61B 17/0057; A61B 17/0487; A61B 17/08; A61B 17/083; A61B 17/10; A61B 17/22; A61B 17/122; A61B 2017/00584; A61B 2017/00588; A61B 2017/00623; A61B 2017/00637; A61B 2017/0061; A61B 2017/081; A61B 2017/086
See application file for complete search history.

(56) References Cited

U.S. PATENT DOCUMENTS

| 5,228,451 | A | 7/1993 | Bales et al. |
| 5,976,161 | A | 11/1999 | Kirsch et al. |
| 2005/0143767 | A1* | 6/2005 | Kimura ............. A61B 17/1222 606/158 |
| 2008/0140089 | A1* | 6/2008 | Kogiso ............. A61B 17/122 606/142 |
| 2008/0147112 | A1* | 6/2008 | Sheets ............. A61B 17/00491 606/205 |
| 2008/0255427 | A1* | 10/2008 | Satake ............. A61B 17/08 600/204 |
| 2011/0295281 | A1 | 12/2011 | Mizumoto et al. |

FOREIGN PATENT DOCUMENTS

| CN | 201234986 Y | 5/2009 |
| CN | 2012034986 Y | 5/2009 |

(Continued)

OTHER PUBLICATIONS

Feb. 1, 2016 Office Action issued in Chinese Application No. 201380019410.4.

(Continued)

*Primary Examiner* — David C Eastwood
(74) *Attorney, Agent, or Firm* — Oliff PLC

(57) ABSTRACT

A closure device includes a protruding member that is detachably provided at a distal end of a longitudinal member; a pair of grasping members that are turnable with respect to the protruding member; first and second linear members that are connected to the pair of grasping members; and a holding portion that has an action portion for applying a force in a direction in which the pair of grasping members approach the protruding member and is detachably provided at a distal end of the longitudinal member.

9 Claims, 15 Drawing Sheets

(56) References Cited

FOREIGN PATENT DOCUMENTS

| | | |
|---|---|---|
| CN | 102281825 A | 12/2011 |
| EP | 1829489 A1 | 9/2007 |
| JP | B-3068178 | 7/2000 |
| JP | A-2001-120561 | 5/2001 |
| JP | A-2008-110210 | 5/2008 |
| JP | A-2010-125200 | 6/2010 |
| JP | WO 2010061867 A1 * 6/2010 ............. A61B 17/08 |
| WO | WO 91/13590 | 9/1991 |
| WO | WO 2008/090978 | 7/2008 |
| WO | WO 2011/037817 | 3/2011 |

OTHER PUBLICATIONS

Mar. 11, 2014 Japanese Office Action issued in Application No. 2014-500180 (with English translation).

Jul. 30, 2013 International Search Report issued in PCT/JP2013/068005 (with English translation).

Mar. 31, 2016 Extended European Search Report issued in Application No. 13832116.1.

* cited by examiner

CLOSURE DEVICE

This application is a continuation based on U.S. Patent Application No. 61/694,935 provisionally applied in the United States on Aug. 30, 2012 and PCT/JP2013/068005, filed on Jul. 1, 2013. The contents of both the United States Patent Application and the PCT Application are incorporated herein by reference.

TECHNICAL FIELD

The present invention relates to a closure device for closing up a perforation formed in living body tissue.

BACKGROUND ART

In the related art, treatment tools that grip living body tissue to perform various kinds of treatment have been studied.

For example, in a grasping device described in Japanese Unexamined Patent Application, First Publication No. 2010-125200, an inner cylinder pipe is inserted into an outer cylinder pipe in a freely insertable manner, and an operating shaft is inserted through the inner cylinder pipe.

One end of a supporting member is anchored to a distal end of the operating shaft. A columnar body configured below a fixing clip is fitted into the supporting member. A combined state of the supporting member and the columnar body is released if both are slightly strongly pulled. A ring-shaped clip control body that abuts against a distal end of the inner cylinder pipe is provided inside the outer cylinder pipe.

The fixing clip is a plate-shaped body as a whole, and the aforementioned columnar body is formed integrally with a lower end of the fixing clip. A pair of movable clips are provided on both sides across the fixing clip. A root portion of each movable clip is anchored to a root portion of the fixing clip by welding. Each movable clip is made of materials having elasticity, and is biased in a direction in which the clip is opened with respect to the fixing clip. The root portion of each movable clip is provided with a protruding portion that overhangs outward. Each protruding portion is provided so as to be slightly shifted in a longitudinal direction of the fixing clip.

In the grasping device configured in this way, the outer cylinder pipe is pulled down with respect to the inner cylinder pipe, whereby the fixing clip and each movable clip are exposed from a distal end of the outer cylinder pipe, and each movable clip is opened. If the operating shaft is pulled down with respect to the inner cylinder pipe, the supporting member attached to the operating shaft also moves downward. According to the supporting member, the fixing clip and each movable clip also move downward. As the operating shaft is pulled down, the fixing clip and each movable clip move downward inside a central hole of the clip control body. However, as the protruding portion provided at a lower portion abuts against the edge of the central hole, the movable clip provided with the protruding portion moves to the fixing clip side, and holds one side portion of a large slit of tissue.

If the operating shaft is further pulled down, the other movable clip is moved to the fixing clip side by the same mechanism, and the other side portion of the slit is held. If the operating shaft is further pulled, the columnar body of the fixing clip slips out of the supporting member. Accordingly, the fixing clip and each movable clip remain inside the body in a state where the respective movable clips holding the side portions of the slip are biased in a direction in which the clip control body is closed.

Additionally, a grasping tool that grips stomach tissue is disclosed in Japanese Unexamined Patent Application, First Publication No. 2008-110210. A shaft and a pair of grasping jaw members are included in the grasping tool. Each grasping jaw member has a plurality of gear teeth. The gear teeth are configured so as to grip tissue. Each grasping jaw members is operable so as to be opened and closed via a cable.

SUMMARY OF THE INVENTION

According to a first aspect of the present invention, a closure device includes a first longitudinal member which extends along a longitudinal axis; a second longitudinal member which extends along the longitudinal axis so as to be movable relative to the first longitudinal member; a protruding member which is detachably provided at a distal end of the first longitudinal member; a pair of grasping members which are provided at the protruding member and intersects with the protruding member, and which includes a distal end portion and an intermediate portion, wherein the distal end portion is capable of grasping tissue between the pair of grasping members and the protruding member, and the intermediate portion is supported so as to be turnable with respect to the protruding member; a first linear member which is connected to a first grasping member that is configured by the pair of grasping members and which extends along the longitudinal axis; a second linear member which is connected to a second grasping member that is configured by the pair of grasping member and which extends along the longitudinal axis so as to be movable relative to the first linear member; an operating portion which is provided at a proximal end of the first longitudinal member and is capable of operating the first linear member and the second linear member so as to move the first linear member and the second linear member relatively; and a holding portion that has an action portion for applying a force in a direction in which a proximal end of the first grasping member and a proximal end of the second grasping member approach the protruding member, is provided at a distal end of the second longitudinal member, and is capable of attaching to or removing from the distal end of the second longitudinal member together with the pair of grasping members.

According to a second aspect of the present invention in the first aspect, the holding portion may be formed in the shape of a tube, the action portion may be an inner peripheral surface of the holding portion, the pair of grasping members may be closed by applying a force to portions of the pair of grasping members that has come into contact with the inner peripheral surface toward a central axis of the holding portion, and a concave-convex portion may be formed on the inner peripheral surface of the holding portion on a cross-section including the central axis of the holding portion.

According to a third aspect of the present invention in the second aspect, the inner peripheral surface of the holding portion may be formed so that the diameter thereof increases toward a distal end side.

According to a fourth aspect of the present invention in the second aspect, the holding portion may include an external member which is formed in a shape of a tube and is provided so as to be capable of attaching to or removing from the distal end of the second longitudinal member; and an internal member which is formed in a shape of a tube, has the concave-convex portion formed on an inner peripheral surface thereof, and is arranged inside the external member. The inner peripheral surface of the external member may be formed so that a diameter thereof increases toward a distal end side. An outer peripheral surface of the internal member is formed so that a diameter thereof increases toward the distal end side.

According to a fifth aspect of the present invention in the fourth aspect, the external member and the internal member may be connected by a ratchet mechanism that allows a movement of the internal member to a proximal end side relative to the external member and regulates the movement of the internal member to the distal end side relative to the external member.

According to a sixth aspect of the present invention in the fourth aspect, an inner diameter of a distal end side of the internal member may be larger than an inner diameter of a proximal end side of the internal member. The inner peripheral surface of the internal member may have a step portion between the distal end side and the proximal end side of the internal member. The concave-convex portion may be formed at the portion of the inner peripheral surface of the internal member closer to the distal end side than the step portion.

According to an seventh aspect of the present invention in any one of the first aspect to the sixth aspect, the pair of grasping members may be supported so as to be turnable around a turning shaft provided at the protruding member, a length from the turning shaft to a distal end of each of the grasping members may be set to be greater than a length from the turning shaft to a distal end of the protruding member, and a distal end of one of the pair of grasping members may be provided with a protruding portion extending toward a distal end of the other of the pair of grasping members.

According to an eight aspect of the present invention in any one of the first aspect to the seventh aspect, the holding portion may be formed of an elastic material.

DESCRIPTION OF EMBODIMENTS

Embodiments

Hereinafter, an embodiment of a closure device related to the present invention will be described, with reference to FIGS. 1 to 20. The closure device is used after being inserted into a channel of an endoscope, and seals perforations formed in tissue of the digestive organs or the like.

Figure 1:
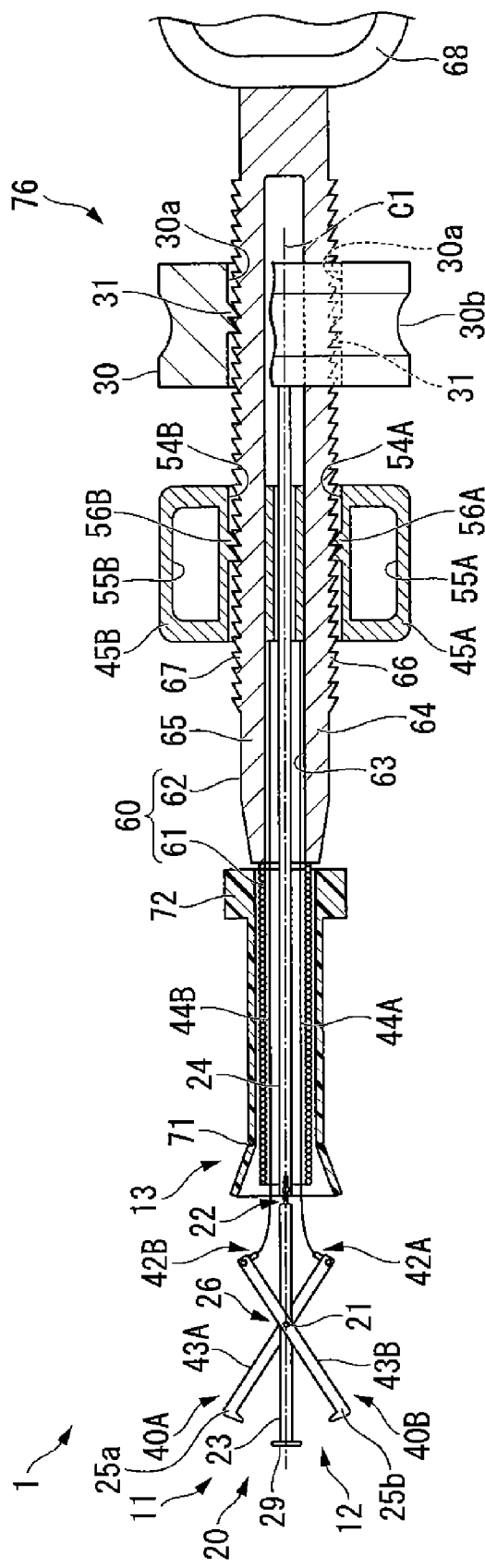
FIG. 1 is a cross-sectional view of a side surface of a closure device of an embodiment of the present invention.
Figure 2:
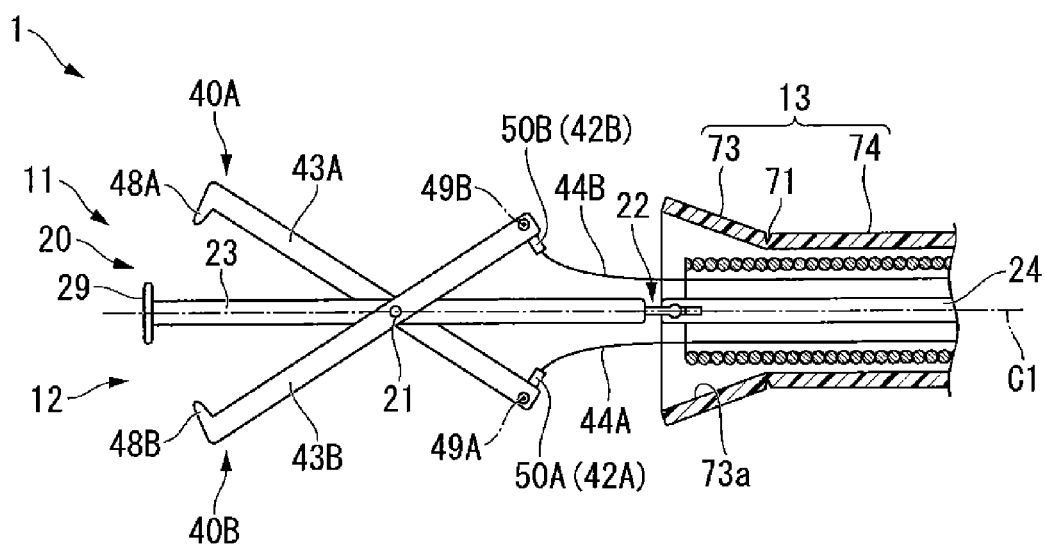
FIG. 2 is an enlarged view of main portions in FIG. 1.

As shown in FIGS. 1 and 2, a closure device 1 of the present embodiment includes a first grasping section 11 and a second grasping section 12 of which distal ends are openably and closably operated, and a holding mechanism 13 for holding a state where the distal end of the first grasping section 11 is closed and a state where the distal end of the second grasping section 12 is closed.

The closure device 1 of the present invention a first longitudinal member 24 which extends along a axis C1 (longitudinal axis); a second longitudinal member 74 which extends along the axis C1 so as to be movable relative to the first longitudinal member 24; an immovable grasping portion (protruding member) 23 which is detachably provided at a distal end of the first longitudinal member 24; a pair of grasping members 43A, 43B which are provided at the immovable grasping portion 23 and intersects with the immovable grasping portion 23, and which includes a distal end portion 25a, 25b and an intermediate portion 26, a first operating wire (first linear member) 44A which is connected to a first grasping member 43A that is configured by the pair of grasping members 43A, 43B and which extends along the axis C1; a second operating wire (second linear member) 44B which is connected to a second grasping member 43B that is configured by the pair of grasping member 43A, 43B and which extends along the axis C1 so as to be movable relative to the first operating wire 44A; an operating portion 45A, 45B which is provided at a proximal end of the first longitudinal member 24 and is capable of operating the first operating wire 44A and the second operating wire 44B so as to move the first operating wire 44A and the second operating wire 44B relatively; and a holding portion 73 that has an action portion for applying a force in a direction in which a proximal end of the first grasping member 43A and a proximal end of the second grasping member 43B approach the immovable grasping portion 23, is provided at a distal end of the second longitudinal member 74, and is capable of attaching to or removing from the distal end of the second longitudinal member 74 together with the pair of grasping members 43A, 43B.

The distal end portion 25a, 25b are capable of grasping tissue between the pair of grasping members 43A, 43B and the immovable grasping portion 23. The intermediate portion 26 is supported so as to be turnable with respect to the immovable grasping portion 23.

In addition, in the description of the present application, a "distal end side" and a "distal end" mean a side near body tissue to be treated or a portion on the side near the body tissue, and a "proximal end side" and a "proximal end" means a side far from the body tissue or a portion on the side far from the body tissue.

The first grasping section 11 has a supporting part 20 that is formed in a rod shape, and a first turning part 40A that is turnably supported around a turning shaft 21 provided on the distal end side of the supporting part 20.

A connecting portion 22 having a lower tensile rigidity in the direction (longitudinal axis) of the axis (central axis) C1 of the supporting part 20 than the other portions of the supporting part 20 is provided at the supporting part 20 closer to the proximal end side than the turning shaft 21. That is, the supporting part 20 is separable into the immovable grasping portion (protruding member) 23 closer to the distal end side than the connecting portion 22 and a first longitudinal member 24 closer to the proximal end side than the connecting portion 22 by pulling both ends of the supporting part 20 in the direction of the axis C1. The first longitudinal member 24 is formed in a shape extending along the axis C1.

Additionally, as will be described below, the supporting part 20 can be again configured by connecting the separated immovable grasping portion 23 and first longitudinal member 24. In this way, the immovable grasping portion 23 is provided at a distal end of the first longitudinal member 24 and is capable of attaching to or removing from the distal end of the first longitudinal member 24.

The immovable grasping portion 23 is provided with the aforementioned turning shaft 21. The immovable grasping portion 23 and the first longitudinal member 24 can be formed of wire rods of stainless steel, a titanium alloy, or the like having biocompatibility and elasticity.

Figure 3:
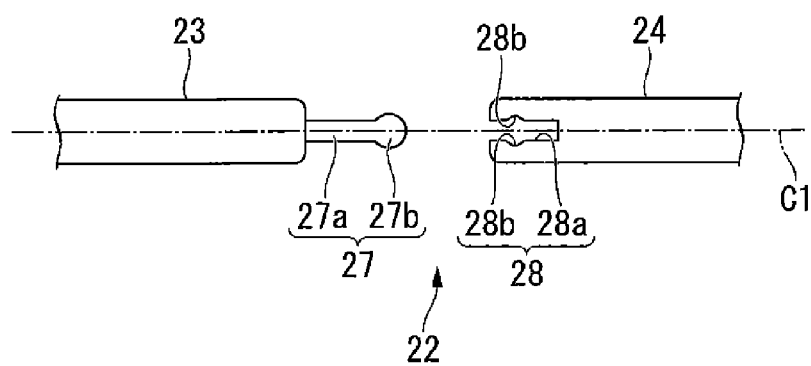
FIG. 3 is a side view illustrating a state where a connecting portion of the closure device is separated.

The connecting portion 22, as shown in FIG. 3, is configured by an engaging portion 27 provided at a proximal end of the immovable grasping portion 23, and an engaged portion 28 provided at the distal end of the first longitudinal member 24.

The engaging portion 27 is configured such that a spherical member 27b made to have a larger diameter than that of a rod-shaped member 27a is fixed to a proximal end of a rod-shaped member 27a that is formed in the shape of a rod extending on the axis C1.

The engaged portion 28 is configured such that a groove portion 28a is provided so as to extend from a distal end surface of the first longitudinal member 24 to the proximal end side, and a pair of recesses 28b are formed on opposing side surfaces inside the groove portion 28a. As the rod-shaped member 27a is arranged within the groove portion 28a and the spherical member 27b is engaged with the pair of recesses 28b, the immovable grasping portion 23 and the first longitudinal member 24 are connected. Additionally, if the supporting part 20 is pulled so that the immovable grasping portion 23 and the first longitudinal member 24 are spaced apart from each other, the groove portion 28a is deformed so that the pair of recesses 28b are spaced apart from each other, and the spherical member 27b is disengaged from the pair of recesses 28b. Accordingly, the immovable grasping portion 23 and the first longitudinal member 24 are configured so as to be separated from each other. The connecting portion configured by making members engage with each other in this way is hereinafter referred to as a "connecting portion formed by engagement".

As shown in FIG. 1, a flat plate-shaped larger-diameter portion 29 extending in a direction orthogonal to the axis C1 is attached to the distal end of the immovable grasping portion 23. A first columnar slider 30 is fixed to a proximal end of the first longitudinal member 24. The first slider 30 is formed with a pair of through-holes 30a extending parallel to the axis C1. The pair of through-holes 30a is formed so as to sandwich the axis C1. A slider claw 31 formed such that a surface on the distal end side is orthogonal to the axis C1 and a surface on the proximal end side is spaced apart from the axis C1 toward the proximal end side is formed on the side of an inner peripheral surface of each through-hole 30a spaced apart from the axis C1. An outer peripheral surface of the first slider 30 is formed with a finger-hooking portion 30b recessed over the whole circumference thereof.

Since the configuration of the first turning part 40A and the configuration of a second turning part 40B to be described below are the same in the present embodiment, the configuration of the first turning part 40A is shown by adding the alphabetic letter "A" to a number, and the configuration of the second turning part 40B is shown by adding the alphabetic letter "B" to the same number. Accordingly, overlapping description will be omitted.

As shown in FIGS. 1 and 2, a connecting portion 42A having a lower tensile rigidity in the direction of the axis C1 than the other portions of the first turning part 40A is provided at the first turning part 40A closer to the proximal end side than the turning shaft 21. That is, the first turning part 40A is separable into a first movable grasping portion (first grasping member) 43A closer to the distal end side than the connecting portion 42A, the first operating wire (first linear member) 44A closer to the proximal end side than the connecting portion 42A, and a first operating portion 45A fixed to the first operating wire 44A by pulling both ends of the first turning part 40A in the direction of the axis C1.

The first movable grasping portion 43A is formed in the shape of a rod (linearly). A distal end of the first movable grasping portion 43A is provided with a protrusion 48A extending toward a distal end of the immovable grasping portion 23. The first movable grasping portion 43A and the protrusion 48A are integrally formed of a material having the same elasticity as the immovable grasping portion 23. The first movable grasping portion 43A is supported by the turning shaft 21 at an intermediate portion in a longitudinal direction thereof so as to be turnable with respect to the immovable grasping portion 23. As will be described below, although the first movable grasping portion 43A grips tissue in cooperation with the first immovable grasping portions 23, it is preferable that the movable grasping portion 43A be easily bent to some extent so that a grasping force grasping the tissue at this time does not become excessively strong.

Figure 4:
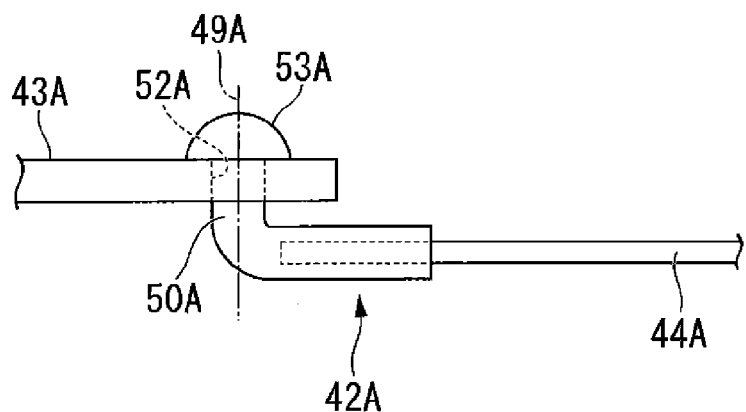
FIG. 4 is a plan view of the connecting portion in a first turning part of the closure device.

As shown in FIGS. 2 and 4, the connecting portion 42A is configured by a tubular member 50A made turnable around an axis 49A parallel to the turning shaft 21 with respect to a proximal end of the first movable grasping portion 43A, and a distal end of the aforementioned first operating wire 44A is crimped to the tubular member 50A.

An opening hole 52A is formed on the axis 49A at the proximal end of the first movable grasping portion 43A. The tubular member 50A is formed by bending an intermediate portion of a tubing material at right angles. The portion of the tubular member 50A closer to the distal end side than the bent portion is inserted through the opening hole 52A. The portion of the tubular member 50A closer to the distal end side rather than the bent portion is provided with a retainer 53A formed with a larger diameter than that of the opening hole 52A. The distal end of the first operating wire 44A is crimped to the portion of the tubular member 50A closer to the proximal end side than the bent portion. The first operating wire 44A is crimped to the tubular member 50A by pressing the tubular member 50A in a radial direction to reduce the diameter thereof in a state where the wire is inserted through a conduit line of the tubular member 50A. It is preferable to use a jig for the crimping so that the force of crimping the first operating wire 44A to the tubular member 50A becomes constant.

Figure 5:
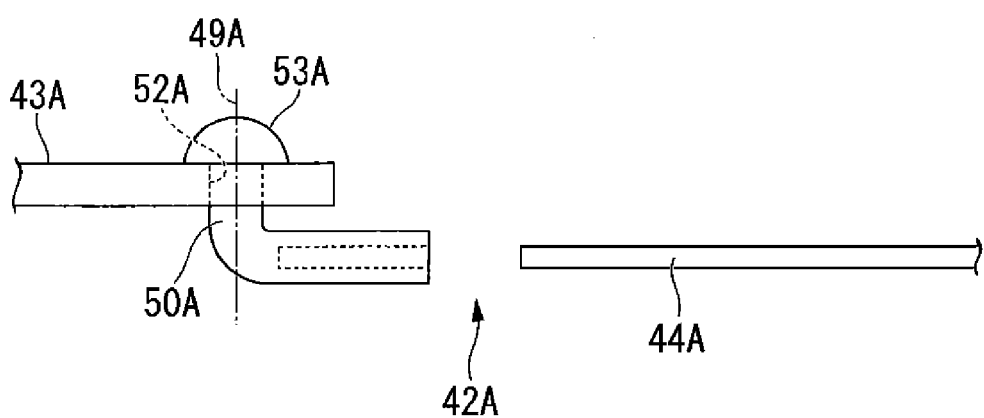
FIG. 5 is a plan view illustrating a state where the connecting portion in the first turning part of the closure device is separated.

In the connecting portion 42A configured in this way, the tubular member 50A is supported so as to be turnable around the axis 49A with respect to the first movable grasping portion 43A. Moreover, if the tubular member 50A and the first operating wire 44A are pulled so as to be spaced apart from each other, the diameter-reduced portion of the tubular member 50A is deformed so that the internal diameter thereof becomes larger. If a pulling force exceeds a constant amount of force, as shown in FIG. 5, the first operating wire 44A is disengaged from the tubular member 50A, and the tubular member 50 and the first operating wire 44A are configured so as to be separated from each other. The connecting portion configured by crimping the members to each other in this way is hereinafter referred to as a "connecting portion formed by crimping".

The first operating wire 44A is formed in a line extending along the axis C1.

As shown in FIG. 1, the first operating portion 45A is fixed to a proximal end of the first operating wire 44A. The first operating portion 45A is formed with a through-hole 54A extending parallel to the axis C1, and a finger-hooking hole 55A for allowing a surgeon's finger to pass therethrough.

An operating claw 56A having the same shape as the slider claw 31 is formed on the side of an inner peripheral surface of the through-hole 54A spaced apart from the axis C1.

The second grasping section 12 has the second turning part 40B supported so as to be turnable around the turning shaft 21. In other words, the second grasping section 12 has the second turning part 40B and the supporting part 20, and the first grasping section 11 and the second grasping section 12 serves also as the supporting part 20.

Although the detailed description of the second turning part 40B is omitted, the second turning part 40B has a configuration corresponding to the connecting portion 42A, the first movable grasping portion 43A, the first operating wire 44A, and the first operating portion 45A of the first turning part 40A, and includes a connecting portion 42B, a second movable grasping portion (second grasping member) 43B, a second operating wire (second linear member) 44B, and the second operating portion 45B.

The portion of the first movable grasping portion 43A closer to the distal end side than the turning shaft 21 and the portion of the second movable grasping portion 43B closer to the distal end side than the turning shaft 21 are arranged opposite to each other with the immovable grasping portion 23 therebetween. Since the movable grasping portions 43A and 43B and the immovable grasping portion 23 are formed in the shape of a straight rod, the portion of the first movable grasping portion 43A closer to the proximal end side than the turning shaft 21 and the portion of the second movable grasping portion 43B closer to the proximal end side than the turning shaft 21 are arranged opposite to each other with the immovable grasping portion 23 therebetween.

The second operating wire 44B and the aforementioned first operating wire 44A can be relatively moved along the axis C1 by operating the operating portions 45A and 45B.

In the present embodiment, as shown in FIG. 1, the operating wires 44A and 44B together with the first longitudinal member 24 are arranged within a main body 60. Specifically, the main body 60 has a coiled sheath 61 arranged at a distal end thereof, and a plate-shaped supporting member 62 attached to a proximal end of the coiled sheath 61. The coiled sheath 61 can be configured, for example, by densely winding a wire formed of stainless steel around the axis C1.

A slit 63 is formed on the axis C1 from a distal end to a central portion in the direction of the axis C1 in the supporting member 62. As the slit 63 passes through the supporting member 62 in a thickness direction, the supporting member 62 is formed with a first rod-shaped portion 64 and a second rod-shaped portion 65 that extend in the direction of the axis C1 with the slit 63 therebetween. A proximal end of the supporting member 62 is formed with a finger-hooking hole 68 that is formed in a ring shape and allows a surgeon's finger to pass therethrough.

A body claw 66 formed such that a surface on the proximal end side is orthogonal to the axis C1 and a surface on the proximal end side is spaced apart from the axis C1 toward the proximal end side is formed on the side of an outer peripheral surface of the first rod-shaped portion 64 spaced apart from the axis C1. Similarly, a body claw 67 formed such that a surface on the proximal end side is orthogonal to the axis C1 and a surface on the distal end side is spaced apart from the axis C1 toward the proximal end side is formed on the side of an outer peripheral surface of the second rod-shaped portion 65 spaced apart from the axis C1.

The first rod-shaped portion 64 is inserted through one through-hole 30a of the first slider 30, and the body claw 66 of the first rod-shaped portion 64 is engaged with the slider claw 31 formed within the one through-hole 30a. Similarly, the second rod-shaped portion 65 is inserted through the other through-hole 30a of the first slider 30, and the body claw 67 of the second rod-shaped portion 65 is engaged with the slider claw 31 formed within the other through-hole 30a.

The portion of the first rod-shaped portion 64 closer to the distal end side than the first slider 30 is inserted through the through-hole 54A of the first operating portion 45A, and the body claw 66 of the first rod-shaped portion 64 is engaged with the operating claw 56A formed within the through-hole 54A. Similarly, the portion of the second rod-shaped portion 65 closer to the distal end side than the first slider 30 is inserted through the through-hole 54B of the second operating portion 45B, and the body claw 67 of the second rod-shaped portion 65 is engaged with the operating claw 56B formed within the through-hole 54B.

As the supporting member 62, the first slider 30, the first operating portion 45A, and the second operating portion 45B are configured in this way, and the first slider 30, the first operating portion 45A, and the second operating portion 45B are movable to the proximal end side with respect to the supporting member 62, respectively, but the movement thereof to the distal end side with respect to the supporting member 62 is regulated by the engagement between the body claws 66 and 67, and the slider claw 31 and the operating claws 56A and 56B.

The holding mechanism 13 is formed of elastic materials such as silicon in the shape of a tube as a whole. As shown in FIGS. 1 and 2, a connecting portion 71 having a lower tensile rigidity in the direction of the axis C1 than the other portions of the holding mechanism 13 is provided on the distal end side of the holding mechanism 13. In this example, the connecting portion 71 is configured by forming a groove in an outer peripheral surface of the holding mechanism 13 over the whole circumference thereof. A second ring-shaped slider 72 formed of metal, such as stainless steel, in the shape of a ring is attached to a proximal end of the holding mechanism 13.

The external diameter of the second slider 72 is formed to be larger than that of the holding mechanism 13 on the proximal end side.

If the holding mechanism 13 is pulled so that a distal end of the holding mechanism and the second slider 72 are spaced apart from each other, the connecting portion 71 is configured so as to be split in the direction orthogonal to the direction of the axis C1 and to be separated into a holding portion 73 closer to the distal end side than the connecting portion 71, and a second longitudinal member 74 closer to the proximal end side than the connecting portion 71. The connecting portion configured by the groove in this way is hereinafter referred to as a "grooved connecting portion".

A longitudinal member is configured by the second longitudinal member 74 and the aforementioned first longitudinal member 24. Also, an operating portion 76 is configured by the first slider 30, the first operating portion 45A, the second operating portion 45B, the finger-hooking hole 68, and the second slider 72.

The holding portion 73 is formed so that the diameters of an inner peripheral surface (action portion) 73a and an outer peripheral surface respectively increase toward the distal end side. In the present embodiment, the inner peripheral surface 73a is formed in the shape of a smooth curved surface.

The second operating wire 44B and the aforementioned first operating wire 44A can be relatively moved along the axis C1 by operating the operating portions 45A and 45B. The first longitudinal member 24 and the second longitudinal member 74 can be relatively moved along the axis C1 independently from each other.

In the closure device 1 configured as described above, the first operating wire 44A is moved to the proximal end side along the axis C1 by moving the first operating portion 45A to the proximal end side with respect to the supporting member 62 from a state where the distal end of the immovable grasping portion 23 and the distal end of the first movable grasping portion 43A, which are shown in FIG. 1, are spaced apart from each other (pulled back). Along with this, the tubular member 50A is turned around the axis 49A, and the first movable grasping portion 43A is turned around the turning shaft 21 so that the distal end of the immovable grasping portion 23 approaches the distal end of the first movable grasping portion 43A (the distal end of the first grasping section 11 is closed). Specifically, the distal end of the first grasping section 11 means the distal ends of the immovable grasping portion 23 and the first movable grasping portion 43A that are relatively turned around the turning shaft 21. As mentioned above, since the movement of the first operating portion 45A to the distal end side with respect to the supporting member 62 is regulated, the first movable grasping portion 43A, which has once approached the distal end of the immovable grasping portion 23, is not turned so that the distal end thereof is separated from the distal end of the immovable grasping portion 23.

Similarly, the second operating wire 44B is moved to the proximal end side by pulling back the second operating portion 45B with respect to the supporting member 62 from a state where the distal end of the immovable grasping portion 23 and the distal end of the second movable grasping portion 43B, which are shown in FIG. 1, are spaced apart from each other. Along with this, the tubular member 50B is turned around the axis 49B, and the second movable grasping portion 43B is turned around the turning shaft 21 so that the distal end of the second movable grasping portion 43B approaches the distal end of the immovable grasping portion 23 (the distal end of the second grasping section 12 is closed). Specifically, the distal end of the second grasping section 12 means the distal ends of the immovable grasping portion 23 and the second movable grasping portion 43B that are relatively turned around the turning shaft 21. The second movable grasping portion 43B is also not turned so as to be separated from the distal end of the immovable grasping portion 23 if the second movable grasping portion has approached the distal end of the immovable grasping portion 23.

As described above, in the closure device 1 of the present embodiment, the distal end of the first grasping section 11 and the distal end of the second grasping section 12 can perform closing operations independently from each other.

Next, a procedure using the closure device 1 will be described. In addition, although a case where a perforation (opening) formed in the stomach wall (tissue) is sealed will be described below, a target part is not limited to this, and may be, for example, hollow organs, such as the esophagus, the duodenum, the small intestine, the large intestine, the womb, and the bladder. Additionally, although an endoscope having a channel through which the closure device 1 is inserted is inserted from a patient's natural opening, this natural opening may be the nose or the anus without being limited to the mouth.

Figure 6:
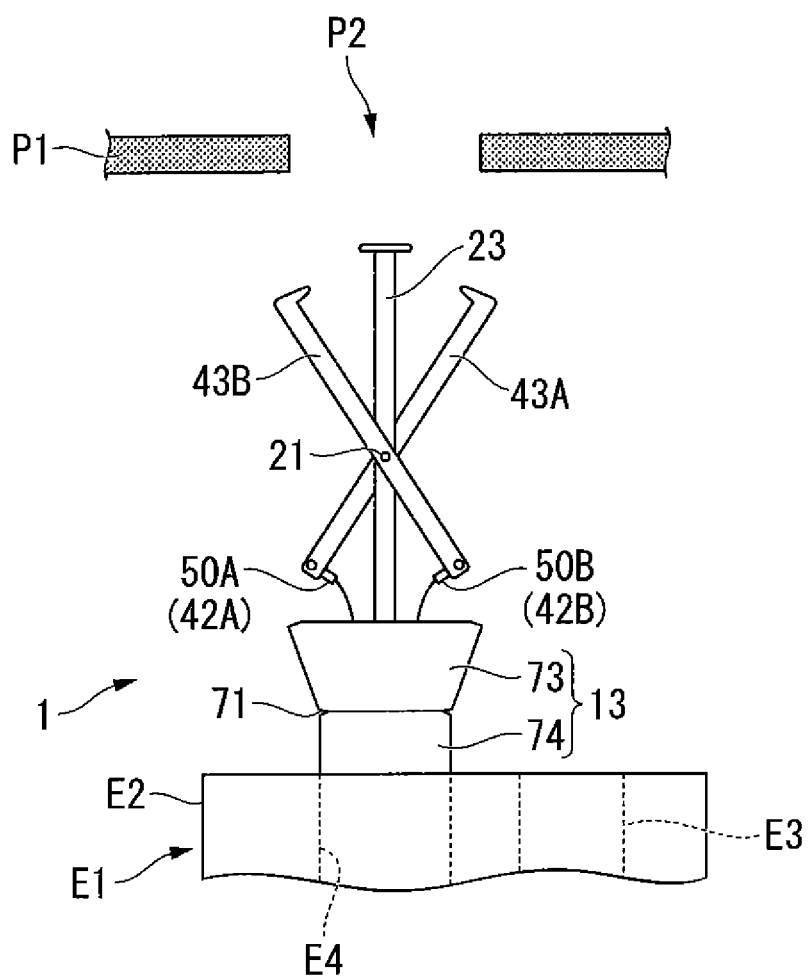
FIG. 6 is a view illustrating a procedure using the closure device.

First, as shown in FIG. 6, an insertion section E2 is introduced to the stomach through a patient's mouth, while observing an image acquired by an observation unit E3 provided at a distal end of the insertion section E2 of an endoscope E1 by a monitor (not shown). In this case, a bending portion (not shown) provided at the insertion section E2 is introduced while being appropriately bent. The bending portion is bent to hold the insertion section E2 in a state where the distal end of insertion section is made to face a perforation P2 formed in a stomach wall P1.

A distal end of the closure device 1 is made to protrude forward from the insertion section E2 through a channel E4 formed in the insertion section E2. Specifically, the immovable grasping portion 23, the movable grasping portions 43A and 43B, and the holding portion 73 of the holding mechanism 13 are made to protrude forward from the channel E4.

Figure 7:
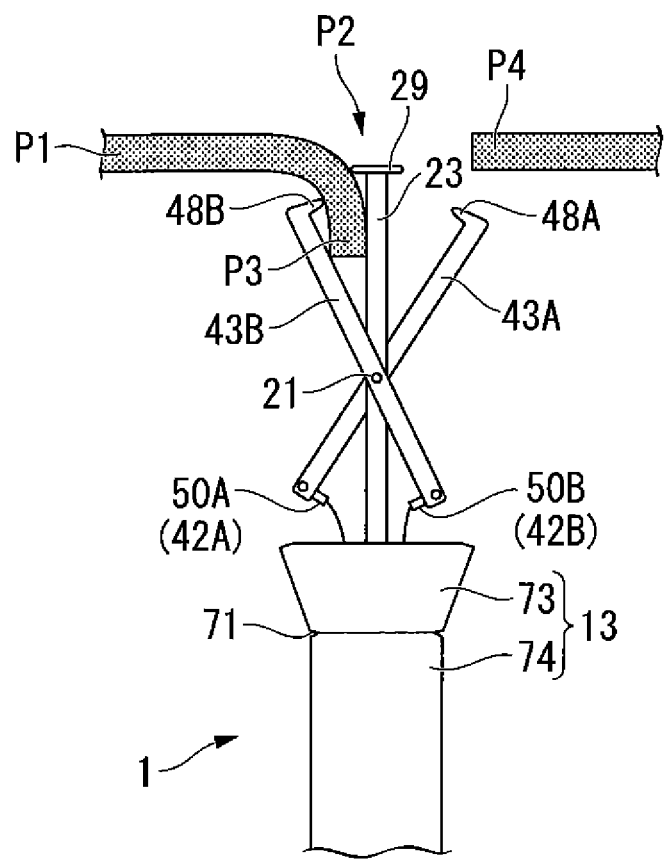
FIG. 7 is a view illustrating a procedure using the closure device.

As shown in FIG. 7, the closure device 1 is moved (pushed) to the distal end side with respect to the insertion section E2, and the side surface of the immovable grasping portion 23 on the distal end side of the second movable grasping portion 43B is made to abut against tissue P3 on one side with respect to the perforation P2 such that the distal end of the tissue P3 is bent to a near side. A surgeon passes his/her thumb through the finger-hooking hole 68 and passes his/her index finger and middle finger through the finger-hooking holes 55A and 55B, respectively, to grip the closure device 1.

If the second operating portion 45B is pulled back, the second movable grasping portion 43B is turned around the turning shaft 21 so that the distal end thereof approaches the distal end of the immovable grasping portion 23, and the tissue P3 is gripped by the immovable grasping portion 23 and the second movable grasping portion 43B. At this time, as the larger-diameter portion 29 provided at the immovable grasping portion 23 and the protrusion 48B provided on the second movable grasping portion 43B bites into the tissue P3, the tissue P3 can be reliably gripped.

Figure 8:
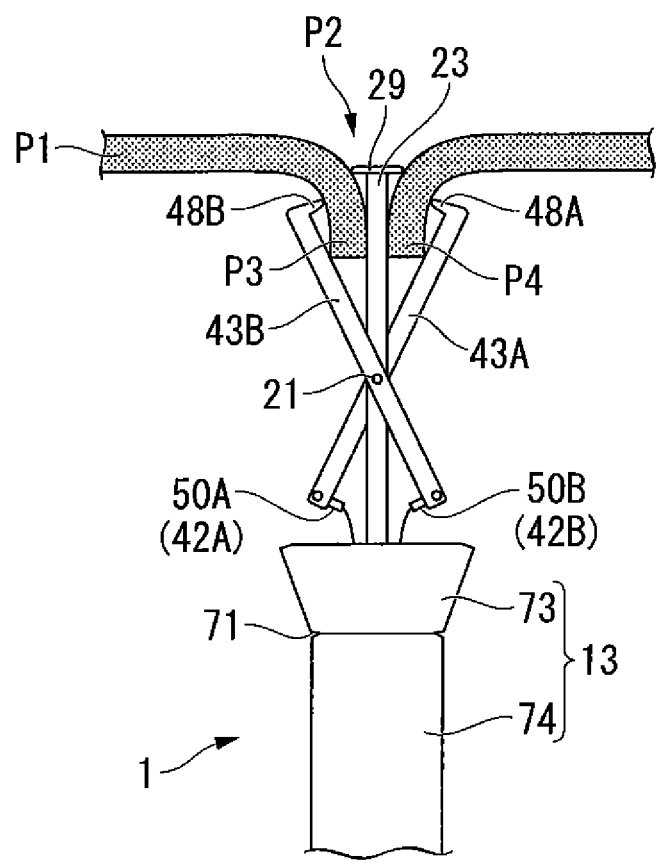
FIG. 8 is a view illustrating a procedure using the closure device.

Subsequently, as shown in FIG. 8, the side surface of the immovable grasping portion 23 on the distal end side of the first movable grasping portion 43A is made to abut against tissue P4 on the other side with respect to the perforation P2 such that the distal end of the tissue P4 is bent to the near side. At this time, the closure device 1 that has gripped the tissue P3 is moved to the tissue P4 side if necessary. Accordingly, even the relatively large perforation P2 can be sealed by drawing the tissues P3 and P4 close to each other.

If the first operating portion 45A is pulled back, the first movable grasping portion 43A is turned around the turning shaft 21 so that the distal end thereof approaches the distal end of the immovable grasping portion 23, and the tissue P4 is gripped by the immovable grasping portion 23 and the first movable grasping portion 43A. At this time, as the larger-diameter portion 29 provided at the immovable grasping portion 23 and the protrusion 48A provided on the first movable grasping portion 43A bites into the tissue P4, the tissue P4 can be reliably gripped.

Figure 9:
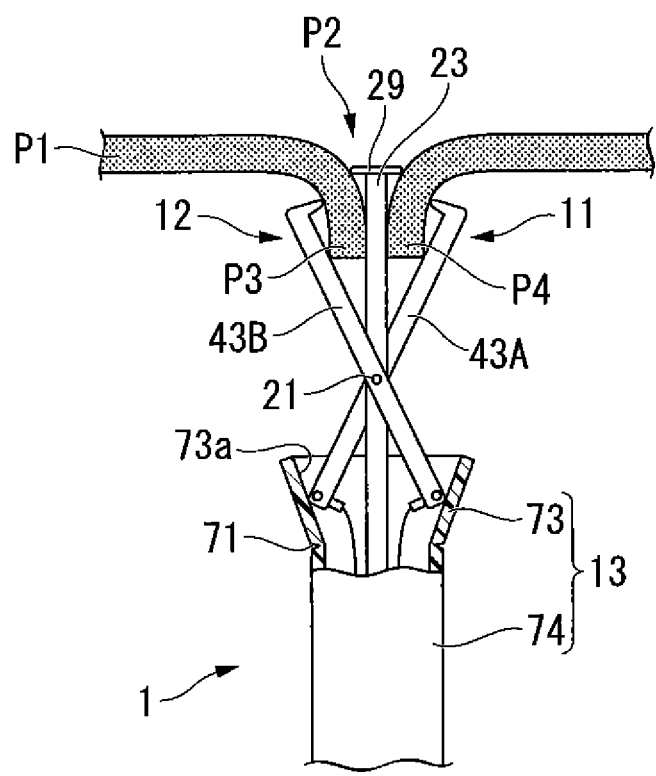
FIG. 9 is a view illustrating a procedure using the closure device.

Next, as the surgeon grips the second slider 72 and pushes in the second slider 72 with respect to the supporting member 62, as shown in FIG. 9, the portions of the movable grasping portions 43A and 43B closer to the proximal end side than the turning shaft 21 are held by the inner peripheral surface 73a of the holding portion 73 of the holding mechanism 13 so as to be sandwiched from the outside. At this time, the inner peripheral surface 73a of the holding portion 73 applies the force of turning the movable grasping portions 43A and 43B around the turning shaft 21 to the portions of the movable grasping portions 43A and 43B on the proximal end side, which have come into contact with the inner peripheral surface 73a. Accordingly, the grasping sections 11 and 12 are moved in closing directions, that is, the distal ends of the movable grasping portions 43A and 43B are moved in directions in which these distal ends approach the distal end of the immovable grasping portion 23.

The inner peripheral surface 73a of the holding portion 73 is formed so that the diameter thereof increases toward the distal end side. Thus, as the second slider 72 is pushed in, a gap between the proximal ends of the movable grasping portions 43A and 43B arranged within the tube hole of the holding portion 73 becomes narrow, and the proximal ends of the movable grasping portions 43A and 43B more strongly come into contact with the inner peripheral surface 73a of the holding portion 73. The holding portion 73 is reliably attached to the proximal ends of the movable grasping portions 43A and 43B by frictional forces applied between the proximal ends of the movable grasping portions 43A and 43B and the inner peripheral surface 73a of the holding portion 73. At the same time, gaps between the distal end of the immovable grasping portion 23 and the distal ends of the movable grasping portions 43A and 43B become narrow, and the tissues P3 and P4 are more strongly gripped by the grasping sections 11 and 12.

Figure 10:
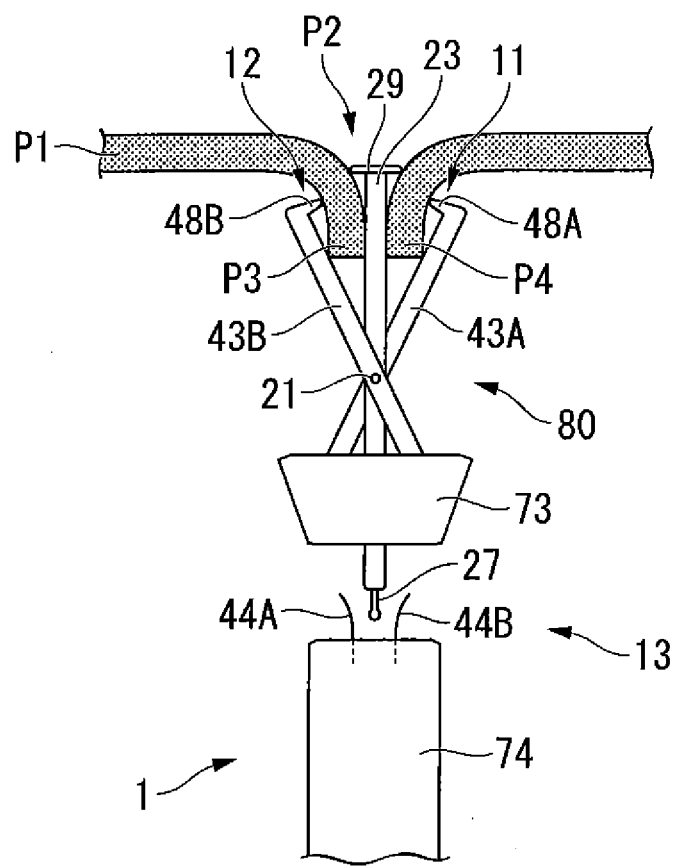
FIG. 10 is a view illustrating a procedure using the closure device.

Here, as the second slider 72 is pulled back, the holding mechanism 13 is pulled so that the holding portion 73 and the second slider 72 are spaced apart from each other, and as shown in FIG. 10, the connecting portion 71 is split and the holding portion 73 and the second longitudinal member 74 are separated from each other.

If the first operating portion 45A is pulled back, the grasping force with which the distal end of the first grasping section 11 grips the tissue P4 increases. If the pulling force of pulling the first operating wire 44A exceeds the aforementioned constant amount of force, the first operating wire 44A is disengaged from the tubular member 50A, and the tubular member 50A and the first operating wire 44A are separated from each other. Similarly, if the second operating portion 45B is pulled back, the grasping force with which the distal end of the second grasping section 12 grips the tissue P3 increases. If the pulling force of pulling the second operating wire 44B exceeds the aforementioned constant amount of force, the second operating wire 44B is disengaged from the tubular member 50B, and the tubular member 50B and the second operating wire 44B are separated from each other.

The first slider 30 is pulled back in a state where the second slider 72 is pushed in to make the distal end of the second longitudinal member 74 abut against the proximal end of the holding portion 73. Then, the immovable grasping portion 23 and the first longitudinal member 24 are pulled so as to be spaced apart from each other, and the immovable grasping portion 23 and the first longitudinal member 24 are separated from each other. In this way, a clip (grip element) 80 configured by the immovable grasping portion 23 separated at the connecting portion 22, the first movable grasping portion 43A separated at the connecting portion 42A, the second movable grasping portion 43B separated at the connecting portion 42B, and the holding portion 73 separated at the connecting portion 71 is placed in a state where the clip has gripped the tissues P3 and P4.

The closure device 1 is pulled out through the channel E4 of the endoscope E1, and the insertion section E2 of the endoscope E1 is taken out from the patient's mouth. If a certain period passes in a state where the clip 80 is placed, the tissues P3 and P4 adhere to each other due to self-restoration, and the perforation P2 is stopped up. The clip 80 naturally falls from the stomach wall P1, and is excreted to the outside of the patient's body.

In the grasping device described in the above Japanese Unexamined Patent Application, First Publication No. 2010-125200, each movable clip can be moved only in a predetermined fixed pattern according to the shape of the protruding portion. Accordingly, in this grasping device, when a perforation formed in tissue is relatively large, there is a problem in that a procedure of closing up the perforation cannot be smoothly performed such that it is necessary to rotate the grasping device around an axis thereof to change the orientation thereof depending on tissue grasping order. As for the grasping instrument described in the above Japanese Unexamined Patent Application, First Publication No. 2008-110210, the respective grasping jaw members are simultaneously opened and closed when the cable is operated. Therefore, there is a problem in that, when a perforation formed in tissue is relatively large, a procedure of closing up the perforation cannot be smoothly performed.

In contrast, according to the closure device 1 of the present embodiment, when the perforation P2 is relatively large and the tissue P3 and the tissue P4 located with the perforation P2 therebetween are separated from each other at a distance, first, the tissue P3 is gripped by pulling back the second operating portion 45B of the operating portion 76 to bring the distal end of the second movable grasping portion 43B close to the distal end of the immovable grasping portion 23. The closure device 1 that has gripped the tissue P3 is moved to the tissue P4 side, and the distal end of the second grasping section 12 is brought close to the tissue P4. The tissue P4 is gripped by pulling back the first operating portion 45A to bring the distal end of the first movable grasping portion 43A close to the distal end of the immovable grasping portion 23. Then, the state of the grasping sections 11 and 12 of which the distal ends are closed is held by pushing in the holding mechanism 13. In this way, as the distal end of the first grasping section 11 pulls back the first operating portion 45A and the distal end of the second grasping section 12 pulls back the second operating portion 45B, closing operations can be performed independently of each other. Accordingly, even in a case where the perforation P2 is relatively large, the perforation P2 can be easily sealed.

The supporting part 20 is provided with the connecting portion 22, the first turning part 40A is provided with the connecting portion 42A, the second turning part 40B is provided with the connecting portion 42B, and the holding mechanism 13 is provided with the connecting portion 71. For this reason, the clip 80 can be separated from the closure device 1 by pulling the supporting part 20, the first turning part 40A, the second turning part 40B, and the holding mechanism 13 in the direction of the axis C1 to separate the closure device 1 at the connecting portions 22, 42A, 42B, and 71. Then, the clip 80 that has gripped the tissues P3 and P4 can be placed inside the patient's body.

The longitudinal member is configured by the first longitudinal member 24 and the second longitudinal member 74. For this reason, separating the immovable grasping portion 23 from the first longitudinal member 24 and separating the holding portion 73 from the second longitudinal member 74 can be separately performed by moving the first longitudinal member 24 and the second longitudinal member 74 along the axis C1.

The inner peripheral surface 73a of the holding portion 73 is formed so that the diameter thereof increases toward the distal end side. Thus, as the holding portion 73 is pushed in, the proximal ends of the movable grasping portions 43A and 43B are more strongly brought into contact with the inner peripheral surface 73a of the holding portion 73. Accordingly, the holding portion 73 can be reliably attached to the proximal ends of the movable grasping portions 43A and 43B.

The holding portion 73 formed by being separated from the holding mechanism 13 is formed of an elastic material. For this reason, the holding portion 73 sandwiching the proximal ends of the movable grasping portions 43A and 43B from the outside can be elastically deformed so as to wrap the proximal ends of the movable grasping portions 43A and 43B, and the state of the grasping sections 11 and 12 of which the distal ends are closed can be more reliably held.

Since the amount of force with which the connecting portions 42A and 42B are separated is adjusted so as to become constant, tissue with various thicknesses can be held with a fixed grasping force.

In addition, the configuration of the closure device 1 of the present embodiment can be variously deformed as described below.

Figure 11:
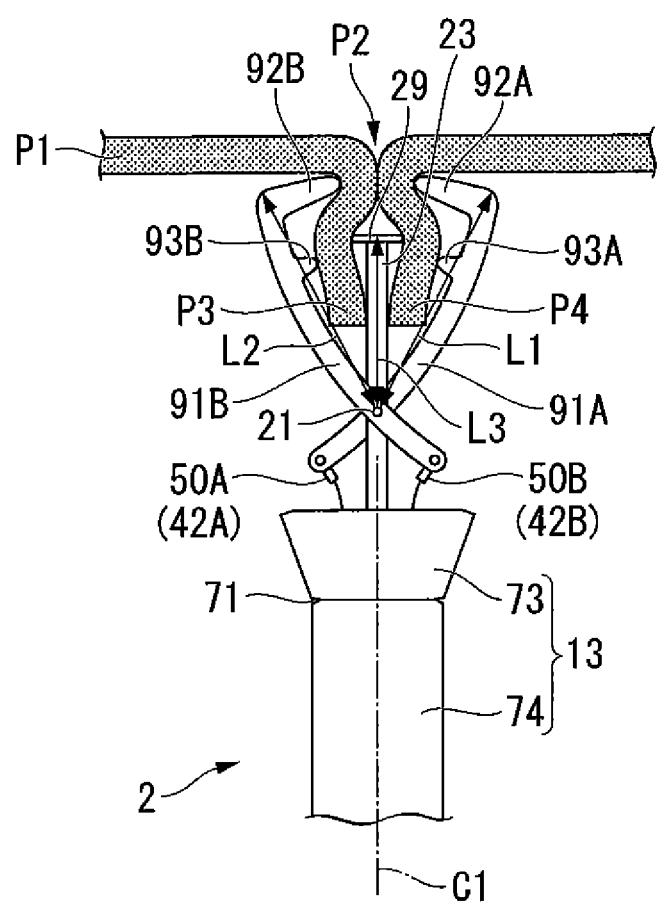
FIG. 11 is a side view of a distal end of a closure device in a modification example of the embodiment of the present invention.

For example, as in a closure device 2 shown in FIG. 11, a length L1 from the turning shaft 21 to a distal end of a first movable grasping portion 91A and a length L2 from the turning shaft 21 to a distal end of a second movable grasping portion 91B may each be greater than a length L3 from the turning shaft 21 to the distal end of the immovable grasping portion 23. In this modification example, the first movable grasping portion 91A is formed in a curved shape.

The distal end of the first movable grasping portion 91A is provided with a protruding portion 92A extending toward the distal end of the second movable grasping portion 91B. An intermediate portion of the first movable grasping portion 91A in a longitudinal direction is provided with a second protruding portion 93A extending in the same direction as the protruding portion 92A. The second movable grasping portion 91B is also provided with the same protruding portion 92B and second protruding portion 93B as the protruding portion 92A and the second protruding portion 93A of the first movable grasping portion 91A.

In the closure device 2 configured in this way, if the operating portions 45A and 45B are pulled back, the movable grasping portions 91A and 91B are turned so that distal ends of thereof approach the distal end of the immovable grasping portion 23, and grip the tissues P3 and P4. In this case, since the lengths L1, L2, and L3 are set as mentioned above and the protruding portions 92A and 92B are provided, portions of the tissues P3 and P4 are brought into close contact with each other without sandwiching the immovable grasping portion 23 therebetween. For this reason, the time taken for the tissues P3 and P4 to adhere to each other can be shortened.

Additionally, since the second protruding portions 93A and 93B are provided, the tissues P3 and P4 can be reliably gripped as the second protruding portions 93A and 93B bite into the tissues P3 and P4.

Figure 12:
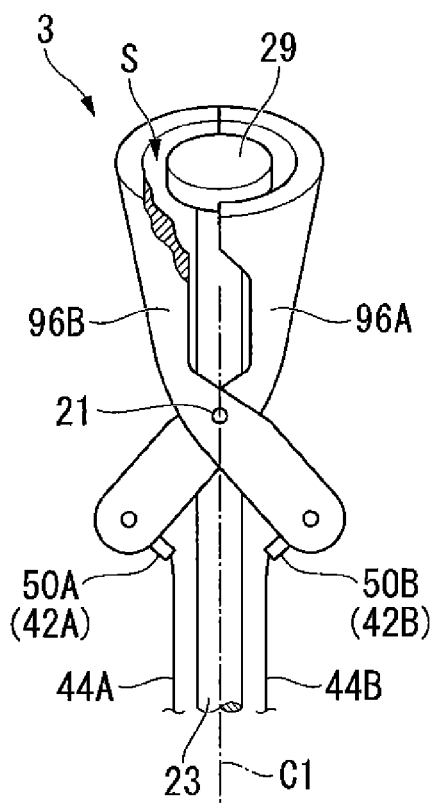
FIG. 12 is a partially cutaway perspective view of a distal end of a closure device in a modification example of the embodiment of the present invention.
Figure 13:
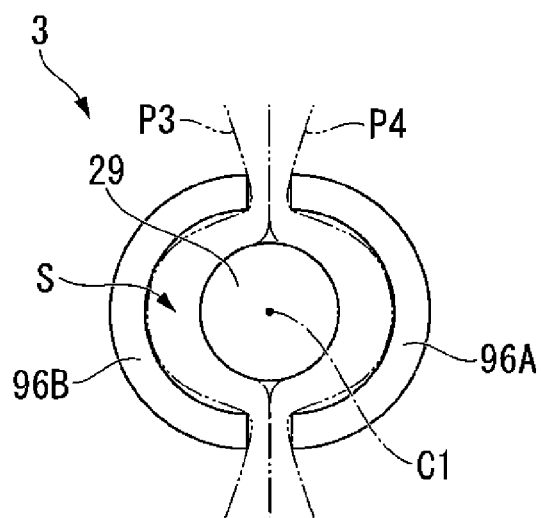
FIG. 13 is a front view of the distal end of the closure device.

As in a closure device 3 shown in FIGS. 12 and 13, when movable grasping portions 96A and 96B have abutted against each other, a gap S may be formed between the immovable grasping portion 23 and the larger-diameter portion 29, and the movable grasping portions 96A and 96B over the whole circumference thereof. In this modification example, distal ends of the movable grasping portions 96A and 96B are formed in the shape of a curved circular arc so as to become convex toward a direction away from the axis C1. Additionally, the radius of the movable grasping portions 96A and 96B formed in the shape of a circular arc is set so as to become smaller toward the proximal end side. The movable grasping portions 96A and 96B are formed in a substantially conical shape as a whole.

In the closure device 3 configured in this way, in FIG. 13 in which a state where the movable grasping portions 96A and 96B have gripped the tissues P3 and P4 is viewed in the direction of the axis C1, the tissues P3 and P4 that are located in the vicinity of circumferential ends of the movable grasping portions 96A and 96B are brought into close contact with each other. For this reason, the time taken for the tissues P3 and P4 to adhere to each other can be shortened.

Figure 14:
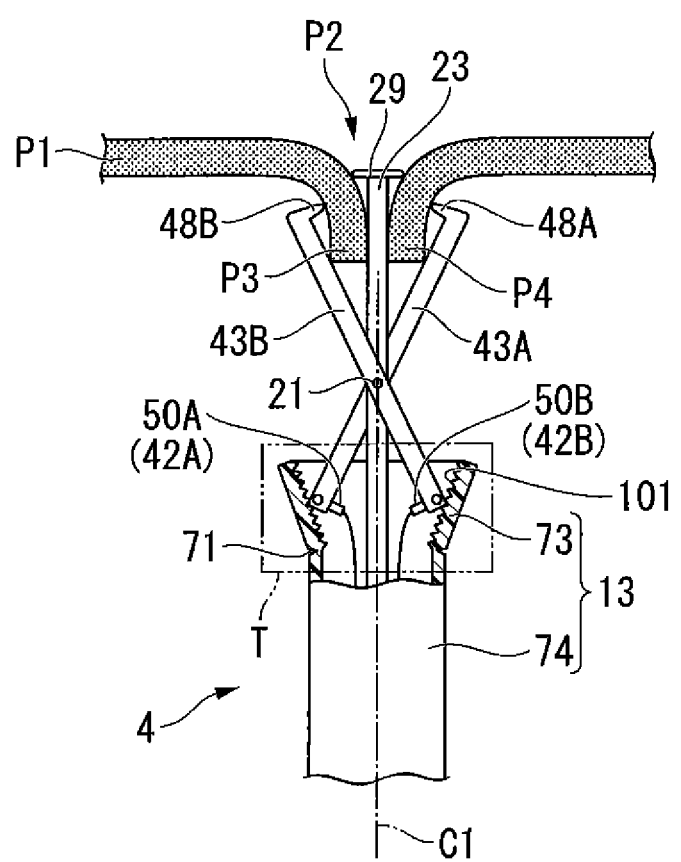
FIG. 14 is a partially cutaway side view of a distal end of a closure device in a modification example of the embodiment of the present invention.

As a closure device 4 shown in FIG. 14, a concave-convex portion 101 in which fine irregularities are provided on an inner peripheral surface of the holding portion 73 from the distal end side to the proximal end side may be formed on a cross-section T including the axis C1 of the holding portion 73. The level difference of the irregularities in the concave-convex portion 101 is preferably 0.1 mm or greater and 1.0 mm or less, for example, when being shown by arithmetic mean roughness Ra. As a material having a small level difference of the concave-convex portion 101, for example, a material having fine irregularities like the surface of sandpaper can be used. It is preferable that proximal ends of the movable grasping portions 43A and 43B be provided with corners in which the interior angle of distal ends is set to about 120 degrees or less or be provided with irregularities comparable with the fine irregularities provided on the concave-convex portion 101.

In the closure device 4 configured in this way, when the holding portion 73 is pushed in to engage the inner peripheral surface 73a of the holding portion 73 with the proximal ends of the movable grasping portions 43A and 43B, the proximal ends of the movable grasping portions 43A and 43B are engaged with the concave-convex portion 101. Accordingly, frictional forces between the inner peripheral surface 73a of the holding portion 73 and the proximal ends of the movable grasping portions 43A and 43B are increased. Accordingly, the holding portion 73 can be more reliably attached to the proximal ends of the movable grasping portions 43A and 43B.

Figure 15:
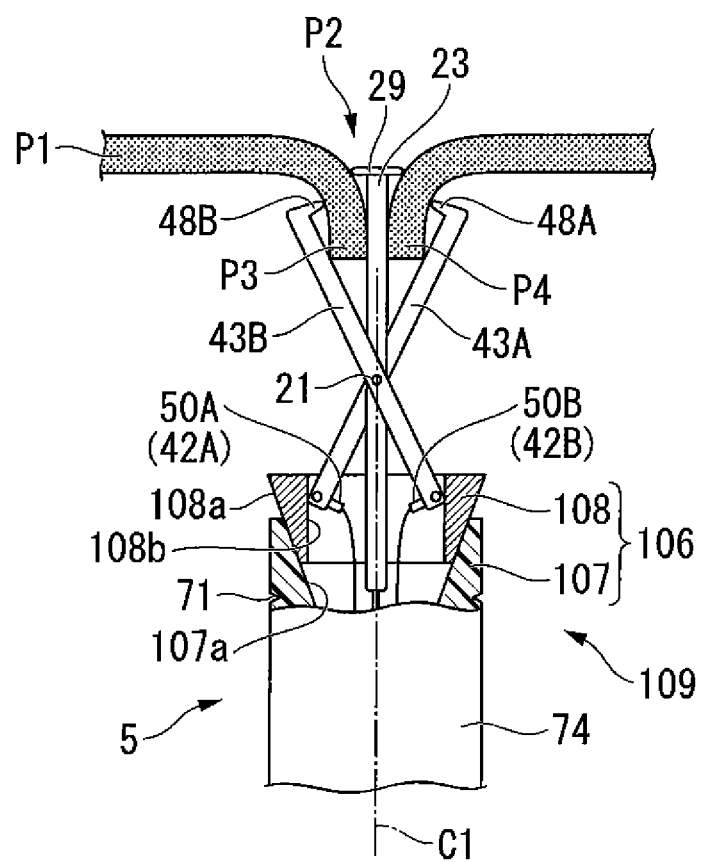
FIG. 15 is a partially cutaway side view of a distal end of a closure device in a modification example of the embodiment of the present invention.

In a closure device 5 shown in FIG. 15, a holding portion 106 has an external member 107 formed in the shape of a tube and an internal member 108 formed in the shape of a tube and is arranged inside the external member 107.

An inner peripheral surface 107a of the external member 107 is formed so that the diameter thereof increases toward the distal end side. A proximal end of the external member 107 is connected to the second longitudinal member 74 via the aforementioned connecting portion 71. An outer peripheral surface 108a of the internal member 108 is formed so that the diameter thereof increases toward the distal end side. The internal diameter of the internal member 108 is set to be equal irrespective of positions in the direction of the axis C1. In this modification example, the inner peripheral surface 107a of the external member 107, the outer peripheral surface 108a and an inner peripheral surface 108b of the internal member 108 are formed in the shape of a smooth curved surface.

The external member 107 and the internal member 108 are respectively formed of elastic materials, such as silicon. The external member 107 is configured so as to have a higher rigidity than that of the internal member 108, that is, so as not to be easily deformed. Specifically, the elastic modulus of a material that forms the external member 107 may be made greater than the elastic modulus of a material that forms the internal member 108, or the external member 107 is configured so as to be thicker than the internal member 108.

In a holding mechanism 109 configured to have the holding portion 106 and the second longitudinal member 74, only a proximal end of the internal member 108 is engaged with the external member 107 before the movable grasping portions 43A and 43B grip the tissues P3 and P4.

In the closure device 5 configured in this way, the holding mechanism 109 is pushed in after the tissues P3 and P4 are gripped by the immovable grasping portion 23 and the movable grasping portions 43A and 43B. Then, the proximal ends of the movable grasping portions 43A and 43B are engaged with the internal member 108 by frictional forces applied between the inner peripheral surface 108b of the internal member 108 and the proximal ends of the movable grasping portions 43A and 43B. If the holding mechanism 109 is further pushed in, the internal member 108 is pushed into the external member 107 in a state where the internal member 108 is engaged with the proximal ends of the movable grasping portions 43A and 43B. Since the rigidity of the external member 107 is higher than that of the internal member 108, the internal member 108 is deformed so that the diameter thereof decreases along the inner peripheral surface 107a of the external member 107 as the internal diameter enters the external member 107, and the gap between the proximal ends of the movable grasping portions 43A and 43B is narrowed. Accordingly, the tissues P3 and P4 are more strongly gripped.

Thereafter, when the holding mechanism 109 is pulled back, the connecting portion 71 is split and the external member 107 and the second longitudinal member 74 are separated from each other because the frictional forces applied between the internal member 108 and the movable grasping portions 43A and 43B and a frictional force applied between the internal member 108 and the external member 107 are sufficiently high.

According to the closure device 5 of the present modification example, the same effects as those of the aforementioned embodiment and modification examples can be exhibited. Moreover, as the internal member 108 enters the external member 107, the internal member 108 acts like a wedge, so that a force with which the internal member 108 enters the external member 107 can be decomposed into a force of reducing the diameter of the internal member 108 and the gap between the proximal ends of the movable grasping portions 43A and 43B can be effectively narrowed.

Figure 16:
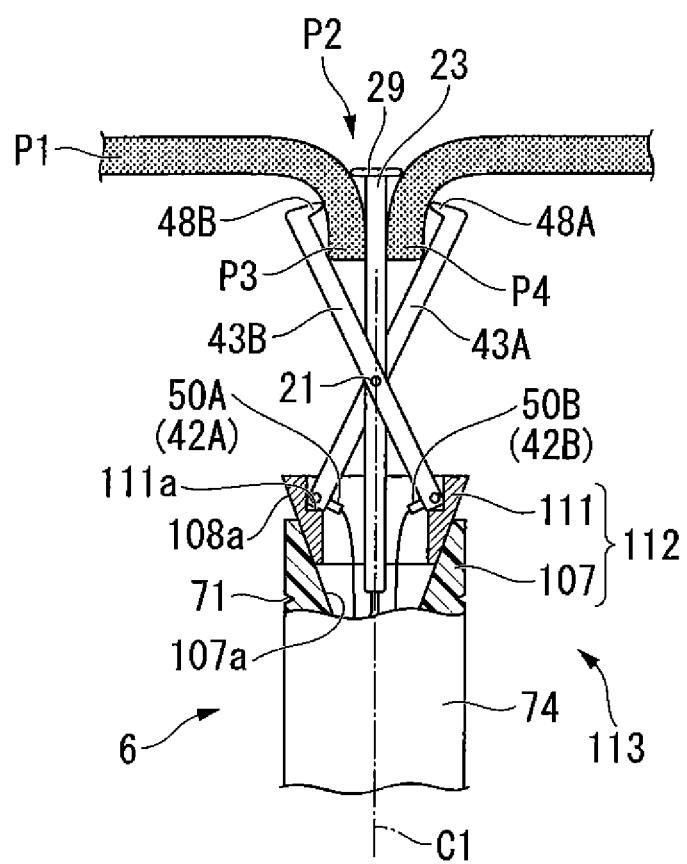
FIG. 16 is a partially cutaway side view of a distal end of a closure device in a modification example of the embodiment of the present invention.

As in a closure device 6 shown in FIG. 16, the closure device may be configured so as to include an internal member 111 instead of the internal member 108 in the closure device 5 of the modification example. As an inner peripheral surface of the internal member 111 is formed so as to have a larger diameter on the distal end side than on the proximal end side, a step portion 111a is formed at a connecting portion between the distal end side and the proximal end side over the whole circumference.

In addition, a holding portion 112 is configured by the external member 107 and the internal member 111, and a holding mechanism 113 is configured by the holding portion 112 and the second longitudinal member 74.

In the holding mechanism 113 configured in this way, if the closure device 6 is pushed, the proximal ends of the movable grasping portions 43A and 43B are locked to the step portion 111a. For this reason, the proximal ends of the movable grasping portions 43A and 43B are prevented from moving from the step portion 111a to the proximal end side, and the movable grasping portions 43A and 43B are prevented from inclining asymmetrically with respect to the axis C1. Accordingly, the holding portion 112 can be more reliably attached to the proximal ends of the movable grasping portions 43A and 43B.

Figure 17:
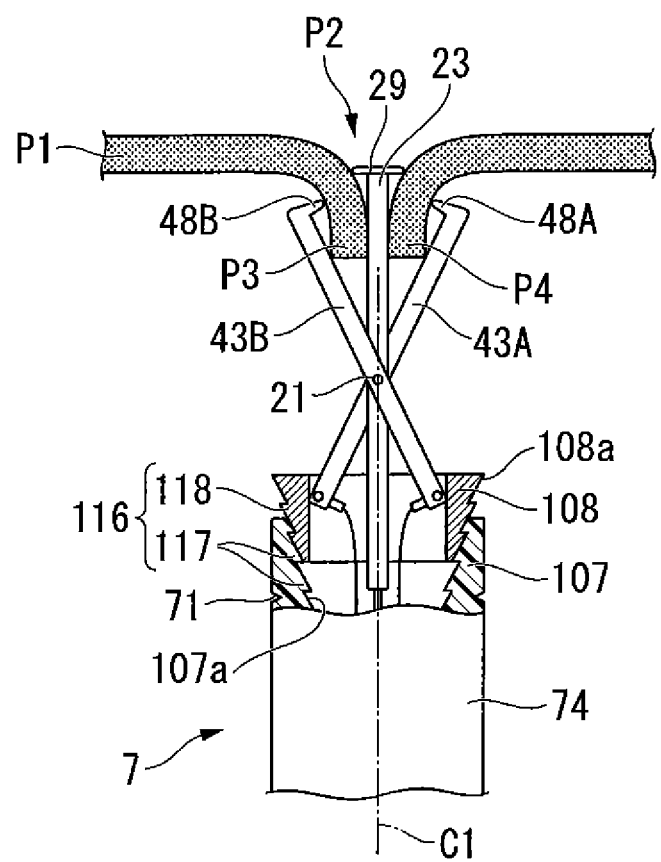
FIG. 17 is a partially cutaway side view of a distal end of a closure device in a modification example of the embodiment of the present invention.

As in a closure device 7 shown in FIG. 17, in the closure device 5 of the modification example, a connecting portion of the external member 107 with the internal member 108 may be provided with a ratchet mechanism 116. In this modification example, the ratchet mechanism 116 is configured by an external claw 117 provided on the inner peripheral surface 107a of the external member 107 and an internal claw 118 provided on the outer peripheral surface 108a of the internal member 108.

The external claw 117 is formed so that a surface on the proximal end side is orthogonal to the axis C1 and a surface on the distal end side is separated from the axis C1 toward the distal end side. The internal claw 118 is formed so that a surface on the distal end side is orthogonal to the axis C1 and a surface on the proximal end side is separated from the axis C1 toward the distal end side.

In the closure device 7 configured in this way, the internal member 108 can be moved to the proximal end side relative to the external member 107 by the engagement between the claws 117 and 118. However, the movement of the internal member 108 to the distal end side relative to the external member 107 can be regulated. For this reason, it is possible to prevent a situation in which the internal member 108 that has moved to the proximal end side with respect to the external member 107 and has entered the external member 107 moves to the distal end side and the movable grasping portions 43A and 43B that have gripped the tissues P3 and P4 are opened.

Although one embodiment of the present invention has been described above in detail with reference to the drawings, specific configuration is not limited to this embodiment, and changes of the configuration are also included without departing from the scope of the present invention.

For example, in the aforementioned embodiment and modification examples, the portions of the inner peripheral surface 108b of the internal member 108 shown in FIG. 15 and the inner peripheral surface of the internal member 111 shown in FIG. 16, which are closer to the distal end side than the step portion 111a, may be formed so that the diameter thereof increases toward the distal end side. By adopting such a configuration, the proximal ends of the movable grasping portions 43A and 43B can be easily engaged with the inner peripheral surfaces of the internal members 108 and 111.

The aforementioned concave-convex portion 101 shown in FIG. 14 may be formed, for example, at the portions of the inner peripheral surface 108b of the internal member 108 and the inner peripheral surface of the internal member 111, which are closer to the distal end side than the step portion 111a. By adopting such a configuration, the frictional forces between these inner peripheral surfaces and the proximal ends of the movable grasping portions 43A and 43B can be increased.

Figure 18:
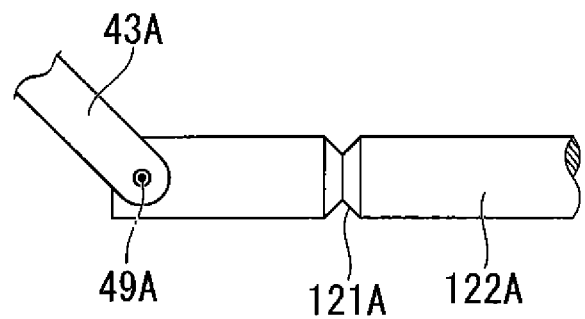
FIG. 18 is a side view of a connecting portion of a first turning part of a closure device in a modification example of the embodiment of the present invention.

A connecting portion 121A as shown in FIG. 18 may be included instead of the connecting portion 42A provided at the first turning part 40A shown in FIGS. 1 and 2. In this modification example, a rod-shaped member 122A is supported by a pin member or the like (not shown) so as to be turnable around the aforementioned axis 49A set at the proximal end of the first movable grasping portion 43A. The connecting portion 121A is configured by a groove formed in an outer peripheral surface of the rod-shaped member 122A over the whole circumference thereof.

Figure 19:
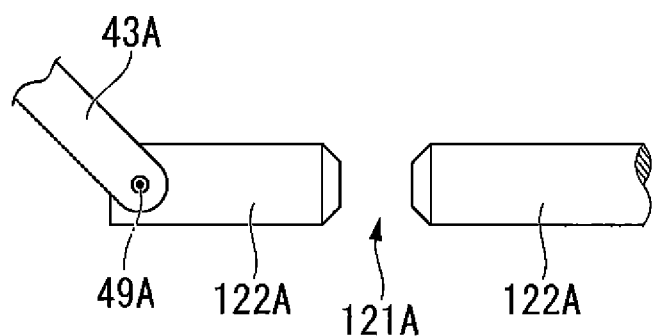
FIG. 19 is a view illustrating a state where the connecting portion is separated.

By pulling the rod-shaped member 122A so that both ends thereof are spaced apart from each other, as shown in FIG. 19, the connecting portion 121A is split in the direction orthogonal to the direction of the axis C1, and the rod-shaped member 122A is separated into two. The connecting portion 42A shown in FIGS. 1 and 2 is the connecting portion formed by crimping, whereas the connecting portion 121A shown in FIG. 18 is the grooved connecting portion. In this way, as the connecting portion between the turning parts 40A and 40B, the grooved connecting portion and the connecting portion formed by engagement may be used instead of the connecting portion formed by crimping. As for the connecting portions of the supporting part 20 and the holding mechanism 13, connecting portions having desired configurations can be also used.

Figure 20:
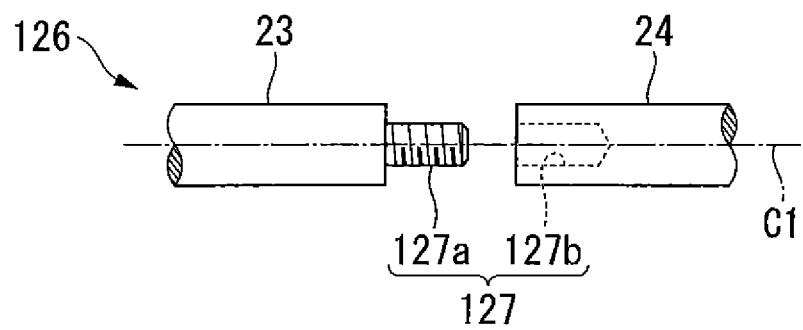
FIG. 20 is a side view of a supporting part of a closure device in a modification example of the embodiment of the present invention.

As a supporting part 126 shown in FIG. 20, an extension mechanism 127 may be provided instead of the connecting portion 22 of the supporting part 20 of the embodiment shown in FIGS. 1 and 2. The extension mechanism 127 has a first threaded portion 127a that is a male thread provided at the proximal end of the immovable grasping portion 23, and a second threaded portion 127b that is a female thread that is provided at the distal end of the first longitudinal member 24 and screwed to the first threaded portion 127a. A closure device is originally in a state where the first threaded portion 127a is screwed to the second threaded portion 127b over the total length thereof. In addition, in this modification example, the first slider 30 shown in FIG. 1 is supported by a well-known mechanism so as to be turnable around the axis C1 with respect to the supporting member 62.

The first slider 30 is rotated with respect to the supporting member 62 shown in FIG. 1, in a state where the position of the supporting member 62 in the direction of the axis C1 is fixed from a state where the first threaded portion 127a shown in FIG. 20 and the second threaded portion 127b are screwed together, and a range where the first threaded portion 127a and the second threaded portion 127b are screwed together is made small. That is, the first longitudinal member 24 is moved to the proximal end side with respect to the immovable grasping portion 23. Then, the first longitudinal member 24, the first slider 30, the supporting member 62, and the operating portions 45A and 45B are integrated by the engagement between the respective claws, and are moved to the proximal end side. Accordingly, the operating wires 44A and 44B shown in FIG. 2 can be pulled to the proximal end side, and the connecting portions 42A and 42B can be separated from each other. Moreover, if the first slider 30 is rotated, the screwing between the first threaded portion 127a and the second threaded portion 127b is released, and the immovable grasping portion 23 and the first longitudinal member 24 are separated from each other. In addition, the first threaded portion 127a may be a female thread and the second threaded portion 127b may be a male thread screwed to this female thread.

In the aforementioned embodiment shown in FIG. 1, the body claws 66 and 67 of the supporting member 62, the operating claw 56A of the first operating portion 45A, and the operating claw 56B of the second operating portion 45B may not be formed. By adopting such a configuration, the first operating portion 45A and the second operating portion 45B are also made movable to the distal end side with respect to the supporting member 62.

If the first operating portion 45A is moved (pushed in) to the distal end side with respect to the supporting member 62, the first movable grasping portion 43A is turned so that the distal end thereof is spaced apart from the distal end of the immovable grasping portion 23 (the distal end of the first grasping section 11 is opened). Similarly, if the second operating portion 45B is pushed in to the distal end side with respect to the supporting member 62, the second movable grasping portion 43B is turned so that the distal end thereof is spaced apart from the distal end of the immovable grasping portion 23 (the distal end of the second grasping section 12 is opened). Accordingly, the movable grasping portions 43A and 43B are openably and closably operated independently of each other with respect to the immovable grasping portion 23.

In the aforementioned embodiment, the first grasping section 11 and the second grasping section 12 serve also as the supporting part 20. However, the first grasping section 11 and the second grasping section 12 may respectively include different supporting parts.

Although the first longitudinal member 24 and the second longitudinal member 74 are configured by separate members, the first longitudinal member 24 and second longitudinal member 74 may be integrally configured. In this case, the proximal ends of the movable grasping portions 43A and 43B are configured so as to come into contact with the inner peripheral surface 73a of the holding portion 73 when the operating portions 45A and 45B are pulled back. By pulling back the first longitudinal member 24 and the second longitudinal member 74 that are integrally configured, the connecting portion 22 of the supporting part 20 and the connecting portion 71 of the holding mechanism 13 are nearly simultaneously separated. In addition, the present invention is not limited by the above description and is limited only by the scope of the appended claims.

While preferred embodiments of the present invention have been described, the present invention is not limited to the embodiments. Additions, omissions, substitutions, and other variations may be made to the present invention without departing from the spirit and scope of the present invention. The present invention is not limited by the above description, but by the appended claims.

The invention claimed is:
1. A closure device comprising:
 a first longitudinal member which extends along a longitudinal axis;
 a second longitudinal member which extends along the longitudinal axis so as to be movable relative to the first longitudinal member;
 a protruding member which is detachably provided at a distal end of the first longitudinal member;
 a first grasping member which is provided at the protruding member and intersects with the protruding member, and which includes a first distal end portion and a first intermediate portion, the first distal end portion being configured to grasp tissue in cooperation with the protruding member, and the first intermediate portion being supported so as to be turnable with respect to the protruding member;

a second grasping member which is provided at the protruding member and intersects with the protruding member, and which includes a second distal end portion and a second intermediate portion, the second distal end portion being configured to grasp tissue in cooperation with the protruding member, and the second intermediate portion being supported so as to be turnable with respect to the protruding member;

a first operating portion which is provided at a proximal side of the first longitudinal member, and which is configured to operate the first grasping member;

a second operating portion which is provided at the proximal side of the first longitudinal member, and which is configured to operate the second grasping member independently from the first grasping member;

a turning shaft which supports the first grasping member and the second grasping member such that the first grasping member and the second grasping member are turnable relative to the protruding member, the turning shaft being provided in an orthogonal direction with respect to a longitudinal direction of the first intermediate portion and the second intermediate portion;

a first linear member which is connected to a proximal end of the first grasping member and to a distal end of the first operating portion, and which extends along the longitudinal axis;

a second linear member which is connected to a proximal end of the second grasping member and to a distal end of the second operating portion, and which extends along the longitudinal axis so as to be movable relative to the first linear member; and a holding portion that has an action portion for applying a force in a direction in which the proximal end of the first grasping member and the proximal end of the second grasping member approach the protruding member with respect to the turning shaft, the holding portion being provided at a distal end of the second longitudinal member, and the holding portion being configured to be attached to or removed from the distal end of the second longitudinal member together with the first grasping member and the second grasping member.

2. The closure device according to claim 1, wherein
the holding portion is formed in the shape of a tube,
the action portion is an inner peripheral surface of the holding portion,
the first grasping member and the second grasping member are closed by applying a force to portions of the first grasping member and the second grasping member that have come into contact with the inner peripheral surface toward a central axis of the holding portion, and
a concave-convex portion is formed on the inner peripheral surface of the holding portion on a cross-section including the central axis of the holding portion.

3. The closure device according to claim 2, wherein the inner peripheral surface of the holding portion is formed so that a diameter thereof increases toward a distal end side.

4. The closure device according to claim 2, wherein
the holding portion includes:
an external member which is formed in a shape of a tube and is configured to be attached to or removed from the distal end of the second longitudinal member; and
an internal member which is formed in a shape of a tube, has the concave-convex portion formed on an inner peripheral surface thereof, and is arranged inside the external member,
the inner peripheral surface of the external member is formed so that a diameter thereof increases toward a distal end side, and
an outer peripheral surface of the internal member is formed so that a diameter thereof increases toward the distal end side.

5. The closure device according to claim 4, wherein the external member and the internal member are connected by a ratchet mechanism that allows a movement of the internal member to a proximal end side relative to the external member and regulates the movement of the internal member to the distal end side relative to the external member.

6. The closure device according to claim 4, wherein
an inner diameter of a distal end side of the internal member is larger than an inner diameter of a proximal end side of the internal member,
the inner peripheral surface of the internal member has a step portion between the distal end side and the proximal end side of the internal member, and
the concave-convex portion is formed at the portion of the inner peripheral surface of the internal member closer to the distal end side than the step portion.

7. The closure device according to claim 1, wherein
the first grasping member and the second grasping member are supported so as to be turnable around the turning shaft provided at the protruding member,
a length from the turning shaft to a distal end of each of the first grasping member and the second grasping member is set to be greater than a length from the turning shaft to a distal end of the protruding member, and
a distal end of one of the first grasping member and the second grasping member is provided with a protruding portion extending toward a distal end of the other of the first grasping member and the second grasping member.

8. The closure device according to claim 1, wherein the holding portion is formed of an elastic material.

9. The closure device according to claim 1, wherein a length from a distal end of the first grasping member to the turning shaft and a length from a distal end of the second grasping member to the turning shaft are each greater than a length from an axis which is provided at the proximal end of the first grasping member to the turning shaft and a length from an axis which is provided at the proximal end of the second grasping member to the turning shaft.

* * * * *